United States Patent
Hunter et al.

(10) Patent No.: US 9,588,087 B2
(45) Date of Patent: Mar. 7, 2017

(54) CONTINUOUS MEASUREMENT CHROMATOGRAPHY AND METHOD OF CONTINUOUS STOCHASTIC PERTURBATION CHROMATOGRAPHY

(71) Applicant: Massachusetts Institute of Technology, Cambridge, MA (US)

(72) Inventors: Ian W. Hunter, Lincoln, MA (US); Eli T. Paster, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 204 days.

(21) Appl. No.: 14/521,885

(22) Filed: Oct. 23, 2014

(65) Prior Publication Data

US 2015/0107334 A1   Apr. 23, 2015

Related U.S. Application Data

(60) Provisional application No. 61/894,897, filed on Oct. 23, 2013, provisional application No. 61/916,994, filed on Dec. 17, 2013.

(51) Int. Cl.
| | | |
|---|---|---|
| *G01N 30/16* | (2006.01) | |
| *G01N 30/86* | (2006.01) | |
| G01N 30/68 | (2006.01) | |
| G01N 30/02 | (2006.01) | |
| G01N 30/62 | (2006.01) | |

(52) U.S. Cl.
CPC ............. *G01N 30/16* (2013.01); *G01N 30/68* (2013.01); *G01N 2030/025* (2013.01); *G01N 2030/027* (2013.01); *G01N 2030/167* (2013.01); *G01N 2030/623* (2013.01)

(58) Field of Classification Search
CPC ....... G01N 27/44743; G01N 27/44791; G01N 30/461; G01N 30/16; G01N 30/86; G01N 2030/3046; G01N 2030/3061
See application file for complete search history.

(56) References Cited

U.S. PATENT DOCUMENTS

| | | | |
|---|---|---|---|
| 3,136,616 A | 6/1964 | Thompson | |
| 3,345,858 A | 10/1967 | Fenske | |
| 5,470,479 A * | 11/1995 | Snyder ................... | B01D 59/30 210/198.2 |
| 5,578,111 A | 11/1996 | Reuter | |
| 5,770,087 A | 6/1998 | Reuter | |
| 5,827,945 A | 10/1998 | Arnold | |

(Continued)

FOREIGN PATENT DOCUMENTS

WO   WO 2015/061576 A1   4/2015

OTHER PUBLICATIONS

César et al., "High-sensitivity micro-gas chromatography using stochastic injection techniques", pp. 997-1000, MEMS 2013, Taipei, Taiwan, Jan. 20-24, 2013.*

(Continued)

*Primary Examiner* — David A Rogers
(74) *Attorney, Agent, or Firm* — Hamilton, Brook, Smith & Reynolds, P.C.

(57) ABSTRACT

A method and system for continuous measurement chromatograph involves stochastically modulating a system variable. The sample can be introduced into a chromatography column. The sample introduction can be modulated stochastically. The sample output from the column can be detected and processed with the stochastic input to provide a sample analysis.

17 Claims, 9 Drawing Sheets

(56) References Cited

U.S. PATENT DOCUMENTS

| | | | |
|---|---|---|---|
| 5,922,106 A | 7/1999 | Mowry et al. | |
| 6,907,796 B2* | 6/2005 | Bremer | G01N 30/12 |
| | | | 219/628 |
| 7,749,390 B2 | 7/2010 | Toumi | |
| 7,921,696 B2* | 4/2011 | Takao | F04B 11/0058 |
| | | | 210/101 |
| 8,277,659 B2* | 10/2012 | Sun | G01N 27/44743 |
| | | | 204/452 |
| 8,336,366 B2 | 12/2012 | Roques et al. | |
| 8,758,271 B2 | 6/2014 | Hunter | |
| 9,322,812 B2* | 4/2016 | Angelescu | G01N 30/86 |
| 2010/0261159 A1 | 10/2010 | Hess et al. | |
| 2011/0054354 A1 | 3/2011 | Hunter | |
| 2012/0318672 A1* | 12/2012 | Sun | G01N 27/44743 |
| | | | 204/604 |
| 2014/0291155 A1* | 10/2014 | Kelly | G01N 27/44743 |
| | | | 204/604 |
| 2015/0041396 A1* | 2/2015 | Kelly | B01D 15/24 |
| | | | 210/656 |
| 2015/0204825 A1* | 7/2015 | Angelescu | G01N 30/16 |
| | | | 73/23.41 |

OTHER PUBLICATIONS

Trap, Oliver, "Investigation of modulation parameters in multiplexing gas chromatography", Journal of Chromatography A, 1217 (2010) 6640-6645.*

Agilent 6890 Gas Chromatograph—Maintaining Your GC, Agilent Technologies, 2007.*

Hunter, I.W. and Kearney R.E., "Generation of Random Sequences with Jointly Specified Probability Density and Autocorrelation Functions", *Biol. Cybern.* 47:141-146 (1983).

Notification Concerning Transmittal of International Preliminary Report on Patentability; PCT Application No. PCT/US2014/061979, "Continuous Measurement Chromatography and Method of Continuous Stochastic Perturbation Chromatography," dated May 6, 2016.

Notification of Transmittal of the International Search Report and the Written Opinion of the International Searching Authority, or the Declaration for International; Application No. PCT/US14/61979, "Continuous Measurement Chromatography and Method of Continuous Stochastic Perturbation Chromatography", dated Jan. 12, 2015, consisting of 8 pages.

* cited by examiner

CONTINUOUS MEASUREMENT CHROMATOGRAPHY AND METHOD OF CONTINUOUS STOCHASTIC PERTURBATION CHROMATOGRAPHY

RELATED APPLICATIONS

This application claims the benefit of U.S. Provisional Application No. 61/894,897, filed on Oct. 23, 2013; and claims the benefit of U.S. Provisional Application No. 61/916,994, filed on Dec. 17, 2013. The entire teachings of the above applications are incorporated herein by reference.

BACKGROUND OF THE INVENTION

Chromatography is one of the most widely used techniques for chemical analysis. The chromatographic process has been around for over a century, while commercial instruments for chromatography have been available since the 1950s. One of the drawbacks in the current art of chromatography is that unlike other chemical analysis techniques (spectroscopy, chemical sensors, etc.), chromatography cannot be performed continuously. In the current art, a specific volume of chemical sample is passed through a chromatographic medium such as a column or cavity, and the output of the sample after passage through the medium, recorded over time, is the resulting chromatogram. Under these conditions, a second sample is not introduced to the chromatographic medium until the first sample has completely passed through the column. Often, the medium is then flushed with gas or liquid before a second, new sample is introduced. Accordingly, it can require a few minutes to several hours between consecutive samples on the same chromatography apparatus.

There have been several attempts to develop continuous chromatographic methods. The most common technique is to stagger or separate sample introduction by a known time-delay, using the traditional injection method used in chromatography, such that a series of staggered chromatographs with a similar time delay will be output with known time delays. A second method involves passing the chromatographic medium, such as the column, through a continuous gas. Previous patents for continuous chromatographic systems include the following:

U.S. Pat. Nos. 5,578,111 and 5,770,087 teach a chromatographic process in which the mixture's components can be dissolved and/or dispersed and/or evaporated, while the phases containing the sorption agents move in opposing directions, and the separated components of the mixture held on the sorption agents are recovered after passage through the separation path.

U.S. Pat. No. 7,749,390 B2 teaches a quasi-continuous process for separating binary and multi-substance mixtures by introducing a sample to a unit which consists of a plurality of individual columns bonded to one another in a direction X in a circle, after which the eluents from the respective columns can be discharged from the respective portion of the circle.

U.S. Pat. No. 5,922,106 A teaches a chromatographic process in which small liquid volume of flow from a liquid process stream containing organic compounds is diverted by an automated process to a heated vaporization capillary where the liquid volume is vaporized to a gas that flows to an automated gas chromatograph separation column to chromatographically separate the organic compounds.

U.S. Pat. No. 5,827,945 A teaches a gas flow distribution system accumulates a sample from a sample bearing carrier gas in a micro-accumulator, delivers it using a carrier gas to a gas chromatography column, and supplies a carrier gas to the gas chromatography column to facilitate separation of the sample into sample components and transport the sample components to a mass spectrometer for trace vapor detection and analysis or testing in real time.

U.S. Pat. No. 3,136,616 teaches a chromatographic system that comprises continuously feeding a material having a plurality of components to be separated and a carrier fluid in a period composition wave of constant frequency to the inlet of a chromatographic column, whereby the said components travel through the column in respective waves at different rates, and emerge from the column out of phase with each other.

U.S. Pat. No. 3,345,858 teaches a chromatographic system in which a carrier gas is passed continually through a column that has been pre-saturated with n-paraffin content, which fixed column samples of the analysis mixture are periodically injection into the carrier gas stream.

SUMMARY OF THE INVENTION

Disclosed herein is a method and system for performing chromatography. The method includes introducing a sample into a chromatography column; stochastically modulating at least one sample variable; detecting an output from a detector; and deconvolving the detector output to an impulse response, for example, by processing the detected output with the stochastic input to provide a sample analysis. The system can include a sample introduction port, a carrier gas source, a capillary column in fluid communication with the sample introduction port and the carrier gas source, a detector configured to detect a sample output from the capillary column, and a processor configured to modulate a sample variable with a stochastic input and to process the detected sample output with the stochastic input to provide a sample analysis. The processor can modulate column temperature by modulating a capillary column heater with a stochastic input. The system can include independent heaters for the sample introduction port, the capillary column, and the detector.

The variable modulated can be sample injection. A constant sample volume can be introduced at stochastically timed intervals. A constant volume per unit time can be introduced according to a stochastic binary sequence. Stochastic modulation can include a stochastic sequence ranging from zero to a predetermined value. The sample volume can be varied according to the numerical value of the stochastic sequence. The numerical value can correspond to the total volume introduced. The numerical value can indicate the volume per unit time at which the sample is introduced. The variable modulated can be sample temperature, column temperature, column pressure, and/or a stochastic switching of the sample passing between two or more chromatographic columns or mediums. The column temperature can be modulated by joule heating if the column is made from a metallic material, or by wrapping the column in a resistive heating element if the column is made from another material. Due to the capillary column's low mass, the column's temperature can be modulated rapidly. Sample introduction can be controlled by a plunger. The plunger can be coupled with a linear actuator. The chromatography can be gas chromatography or liquid chromatography.

The chromatographic system can be used to perform continuous chromatography. The method can be applied to existing chromatographic systems to perform continuous analysis.

The methods and systems disclosed herein may improve the ability to continuously analyze and separate a mixture into component chemicals to determine their relative concentrations. They may also be used to control a chromatographic apparatus to reduce the noise in the output signal, thereby resulting in a more sensitive chromatographic measurement.

The device can continuously measure a gas chromatogram. The method of performing chromatography can be used to continuously determine the chemical components of a chemical mixture, the relative concentrations of those components, the retention times of chemicals that interact with a chromatographic medium, and the sensitivity and correlations between the chemical components of a mixture and various apparatus parameters of a chromatograph. The device can use linear and non-linear stochastic signal processing techniques to continuously perturb a chromatographic apparatus while the inputs and the outputs are continuously monitored and recorded by one or more detectors. The detectors can operate in series or parallel. Through various methods of signal processing, the impulse response of the chromatographic system can be determined. The resulting impulse response and the mathematical characteristics of the impulse response curve can correspond to a traditional chromatogram, such as those obtained by the current art. The impulse response can also carry additional information about the properties of the chemical mixture and the individual components of that mixture. For example, running the chromatograph at different temperatures can cause the constituent chemical to elute at different times, thereby causing a shift in retention time, peak width, and resolution. The impulse response can be determined and updated continuously. This method of chromatography can reduce spurious sources of noise present when performing chromatographic analysis. This method is applicable to many different forms of chromatography, including gas, liquid, solid, HPLC, paper, and ion-exchange chromatography. The method is also applicable to 1-dimensional or N-dimension chromatography.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

Figure 1A:
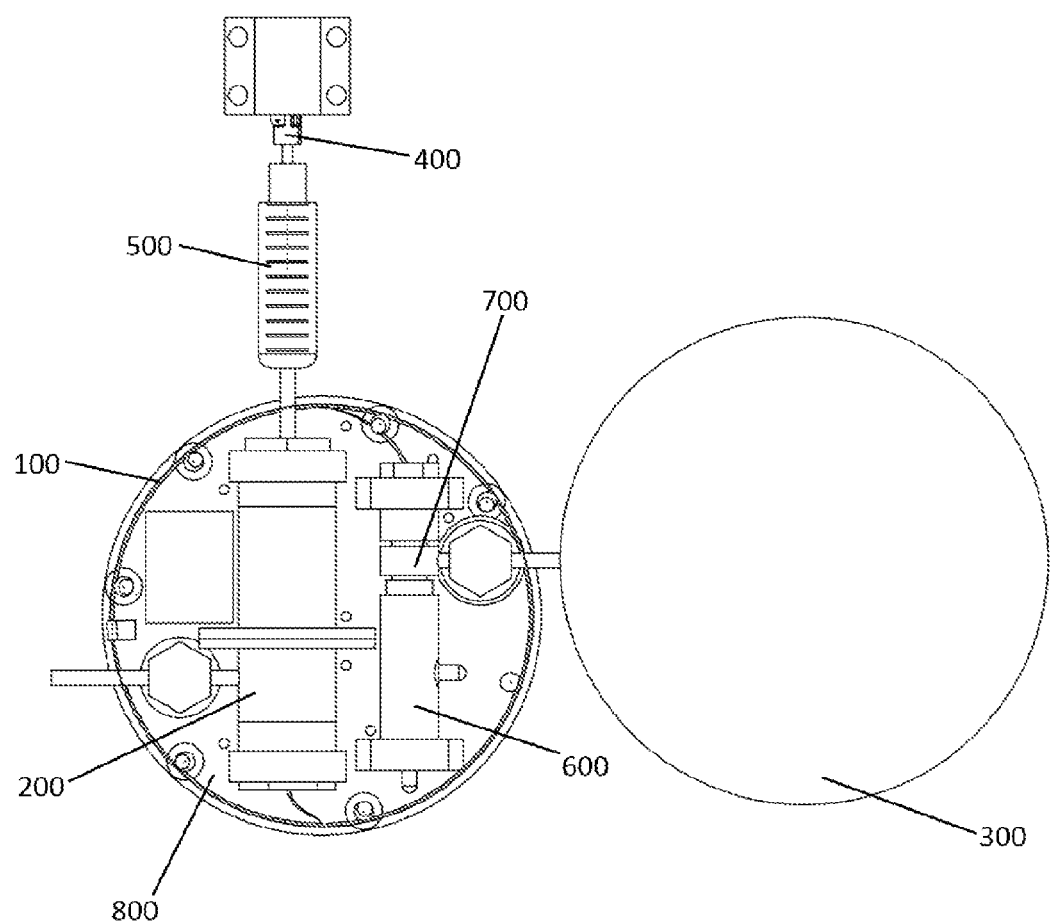
FIG. 1A illustrates a top view of a miniaturized gas chromatograph that can separate eluents using the traditional method of chromatography, or using stochastic perturbation methods.

In the drawings shown, it being understood that the descriptions and drawings are only for the purpose of illustration, and are not intended as a definition of the limits of the invention.

DETAILED DESCRIPTION OF THE INVENTION

Chromatographic methods and instruments can be used to determine the constituent components of a chemical mixture and the relative concentrations of the components. An exemplary chromatographic device includes a chromatographic medium, such as a column or tube; a carrier medium, such as a gas or liquid; a detector, such as a flame-ionization detector, thermal conductivity detector, ultrasonic detector, an electron capture detector, nitrogen phosphorous detector, flame photometric detector, photoionization detector, hall electrolytic conductivity detector, gas density detector, radioactivity detector, helium ionization detector, or any other suitable detector; a controlled sample introduction, such as a displacement controllable syringe or a valve; and a computer or microprocessor that controls the input to the chromatographic system and records the output of the system from the detector or detectors. The input to the system can be a single controlled stochastic sequence or a set of controlled orthogonal stochastic sequences that perturb the system. As used herein, the orthogonal inputs are simply independent variables. These inputs can be a stochastic sequence of sample injections, a stochastic perturbation of the sample or column temperature, or a stochastic perturbation of the column pressure. These inputs can also be a stochastic switching of the sample passing between two or more chromatographic columns, such that the same sample is connected to both columns via a two-way switching valve. If the valve is in a first state, the sample is passed to a first column. If the valve is in a second state, the sample is passed to a second column. These inputs can also be a stochastic switching of multiple samples, such that two sample reservoirs are connected to a single column via a two-way switching valve. If the valve is in a first state, a first sample is passed to the column. If the valve is in a second state, a second sample is passed to the column. The measured response from one or more detectors, along with the measure of the input or inputs, is used to determine the impulse response of the system, which can be used to determine the properties of the chemicals passing through the chromatographic apparatus. In another embodiment, a plurality of sample inputs can be introduced into a column. Each sample input can be independently controlled by a stochastic input that is independent of a stochastic input controlling the other sample inputs. For example, each stochastic input can control the opening and closing of a valve that thereby controls the respective sample inputs.

A stochastic sequence can be a random sequence or a pseudo-random sequence. A sufficiently complex pattern can be sufficiently stochastic over the time scale of the experiment. Whether a pattern is sufficiently stochastic can be determined by auto correlating the pattern with itself to ensure there is no correlation with the sequence. For example, such sequences can be generated with an arbitrary specified first-order probability distribution function and an arbitrary specified first order auto-correlation function. A set of numbers having a desired probability distribution function are generated. These values are given an independent (white) auto-correlation function by double stochastic interchange. The desired auto-correlation function is then obtained by stochastically shuffling the series to minimize a sum of squares criterion between the desired and actual auto-correlation functions.

The methods disclosed herein can be performed by adding instrumentation onto existing chromatographic systems or by specially-designed chromatographic systems that control system inputs.

One mode of stochastic sample introduction can include introducing a constant volume of a sample into the chromatographic column at stochastically timed intervals. Another mode of operation can include introducing a constant volume per unit time into the chromatographic system according to a binary sequence, where zero indicates no sample introduction and one indicates continuous sample introduction at a constant volume per unit time. In another mode of operation, a stochastic sequence can range from zero to a predetermined value, and the volume of the sample introduced into the column can vary according to the numerical value of the sequence. For example, the numerical value can indicate the total volume introduced or the volume per unit time at which the sample is introduced.

In one embodiment, sample introduction can be controlled by a plunger of a gas-tight or liquid tight syringe. The plunger can be coupled with a linear actuator, such as a stepper motor, a Lorentz-force actuator, a piezo-electric actuator, a worm gear coupled with a motor, or another form of actuation that moves along a linear path. The actuator, and thus the plunger, can be controlled by a computer or microprocessor.

In another embodiment, sample introduction can be controlled by opening and closing a valve connected to a pressurized gas or liquid sample supply line, such that sample is introduced when the valve is opened, and sample is not introduced when the valve is closed.

In another embodiment, sample introduction can be controlled by opening and closing a valve connected to a pump situated in the environment in which the apparatus is located. In other words, the pump pressurizes the environmental medium, such as a gaseous atmosphere or a body of liquid, enabling the medium to be injected into the system when the valve opens.

The introduced sample can be heated, cooled, or remain at the temperature at which it was injected. The sample can then be introduced to a carrier medium, such as a carrier gas or liquid, that passes through a chromatographic medium. In one embodiment, the sample is introduced to a single column with one medium. In another embodiment, the sample is introduced to multiple columns with one medium. In another embodiment, the sample is introduced to multiple columns with multiple mediums.

The mediums need not be of the same type, and the sample can be heated, cooled, or kept at a constant temperature depending on the medium through which it passes. In one embodiment, a liquid sample at a single injection location can be divided by volume into known ratios. A first portion of the sample then passes, in liquid form, through a first chromatographic medium while a second portion of the sample is vaporized and then passes, in gaseous form, through a second chromatographic medium. This method of multiple mediums and multiple sample states is not limited to two columns, and can involve multiple columns.

The column can be held at a constant temperature or modulated according to a stochastic sequence. In one mode of operation, the temperature can be modulated stochastically between two specified temperatures. In another mode of operation, the temperature is modulated among a set of predetermined temperatures. In another mode of operation, the temperature can be modulated between a lower and upper temperature, whereby the temperature corresponds with the value of a stochastic sequence.

The column can be heated by placing it in an oven, a liquid temperature controlled bath, or a gaseous or liquid chamber that is closed to the atmosphere. The column can also be heated by wrapping the column with spiral wire and heating the wire through resistive heating. The column can also be heated by placing the column in a sheath and heating the sheath. The column can also be heated by depositing metal onto the external surface of the column and heating the external surface of the column using resistive heating. If the column is electrically conductive, the column can also be heated by electrically isolating the column while passing an electrical current through the length of the column.

In one embodiment, a single column can be used as the chromatographic medium. In another embodiment, multiple columns of different types can be used as the chromatographic medium, simultaneously. For example, the interior coating of the column can differ so that the column is optimized to separate different types of compounds. These different columns that are optimized to separate different types of compounds can include column coatings that are specifically used for environmental analysis, flavor or fragrance analysis, petroleum analysis, pharmaceutical analysis, or a variety of other types of analytical separations. In another embodiment, multiple columns of the same type can be used as the chromatographic medium, and the net result is determined by the averaging of the chromatograms from each respective column.

The carrier medium that carries the sample through the chromatographic medium can be a liquid or a gas. The pressure or flow rate of the carrier medium can be stochastically modulated between two specified values using a binary sequence, or it can be stochastically modulated over a wide range of values. Similar operations can deconvolve a system stochastically modulated between two specified values using a binary sequence and a system stochastically modulated over a wide range of values.

The carrier medium can be provided by a source gas, such as from a tank of nitrogen, helium, or hydrogen. In another embodiment, the carrier medium is produced within the apparatus itself, for example by a hydrogen electrolyzer. For liquid chromatography, the carrier medium can be provided by a supply of a liquid carrier medium, such as deionized water, methanol, acetonitrile, or other carriers. The carrier medium can be a mixture of carrier mediums.

The eluents from the column or chromatographic medium are passed through one or more detectors. The output signal from the detector can be used to analyze the sample to provide a sample analysis. For example, the output signal from the detector can be used to analyze the sample to determine the impulse response of the system.

In instances where more than one apparatus parameter is modulated with a stochastic sequence, such as sample introduction, temperature, or pressure, the respective stochastic sequences that determine the modulation of one apparatus parameter may be non-correlated to the other stochastic sequences that determine the modulation of another apparatus parameter. For example, sequences are non-correlated when a cross-correlation of two sequences does not exhibit any distinctive pattern or features.

A method of processing the detected output to provide a sample analysis involves measuring the stochastic input sequence or sequences while measuring the output from one or more detectors. In some cases, the stochastic input sequence need not be measured, so long as the stochastic pattern used to generate the input sequence is known. The sample analysis can be determined through a series of matrix operations described by Equations 1-4. In these equations, the variable P represents the input, the variable O represents the output, the variable n represents the number of samples, the variable $\Delta t$ represents the time interval between each successive sample, the variable h represents the sample analysis or impulse response, and the variables i and j represent indices. The sample analysis can be determined by first creating an autocorrelation of the input function (EQN. 1) and a cross-correlation of the output and input functions (EQN. 2). A Toeplitz matrix can then be formed (EQN. 3) from the auto-correlation of the input function (EQN. 1). Finally, the product of the inverse of the time interval, the inverse Toeplitz matrix, and the cross-correlation matrix yields the impulse response (EQN. 4). When a chromatographic system is perturbed by multiple, independent, stochastic inputs, and the system output is measured by a single detector, the impulse response of each respective input can be determined by utilizing Equations 1-4, where the input variable P corresponds to each respective input and the output variable O corresponds to the single detector output.

$$C_{PP} = \frac{1}{n}\sum_{j=1}^{n-1}(P_{i-j} \cdot P_i) \quad \text{(EQN. 1)}$$

$$C_{PO} = \frac{1}{n}\sum_{j=1}^{n-1}(P_{i-j} \cdot O_i) \quad \text{(EQN. 2)}$$

$$T_{ij} = C_{PP|i-j|} \quad \text{(EQN. 3)}$$

$$h = \frac{1}{\Delta t}T_{ij}^{-1} \cdot C_{PO} \quad \text{(EQN. 4)}$$

Another method involves measuring the system response and then adjusting the length of the stochastic input sequence or sequences according to the results. Another method involves applying various stochastic input sequences, analyzing the results, and then using a smaller subset of sequences to obtain higher accuracy or resolution within the results. One example of this may occur when a specific temperature range produces the desired results. In this case, the input can be shaped by perturbing the system over a smaller range of temperatures than was done initially. Another method involves stochastically perturbing the system, and then changing the perturbation parameters by shaping the input such that specific sections of the chromatographic output are more visible or visibly separated. One example of this may occur when an eluent takes a long time to pass through a column. By changing the perturbation parameters, such that lower frequencies are present in the input sequence, the eluent may be more clearly observed and accurately represented. In general, these methods are referred to in control theory as input shaping.

Stochastically perturbing a chromatographic system can provide several benefits. For example, a continuous chromatograph can be obtained, thereby enabling the chromatograph to be placed directly in an environment or on a processing line, potentially eliminating the need for an operator. The chromatograph can be obtained continuously because the samples are injected into the system without having to wait for the prior samples to clear the system. In other words, a second sample can be injected while the first sample is eluting through the column. Although this results in overlapping peaks in the chromatograph, the overlapping peaks can be deconvolved to result in a single chromatograph. This can also permit an operator to view changes to the chromatograph closer to real time than with a traditional chromatograph.

Spurious noise sources that normally affect a chromatogram can be reduced. The results of each small individual measurement can be superimposed on top of one another in the deconvolved chromatograph, which reduces noise and improves sensitivity.

Automated systems that involve complex electro-mechanical systems can be eliminated, thereby reducing maintenance. The chromatographic output can be improved by tuning the stochastic input sequence. Additional information about the sample and its eluents can be determined, such as sensitivity to temperature and saturation characteristics as a function of temperature and pressure. The system can perform chromatographic analysis in a reduced period of time. Another advantage is that the column length or volume of the chromatographic medium can be reduced.

Figure 1B:
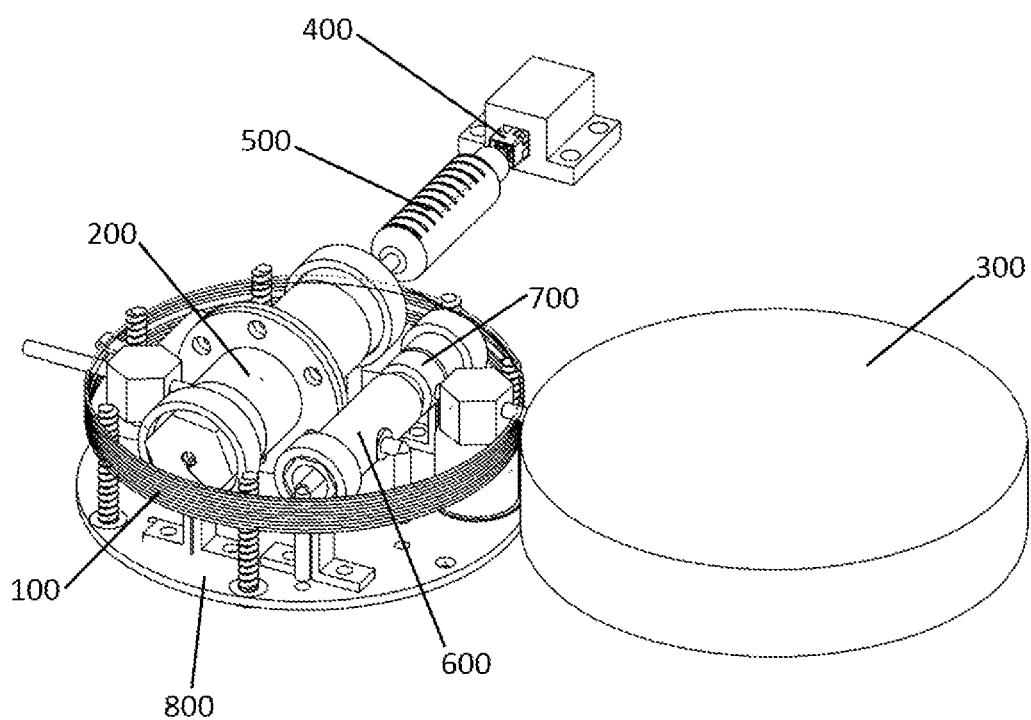
FIG. 1B illustrates an isometric view of the miniaturized gas chromatograph of FIG. 1A.
Figure 7A:
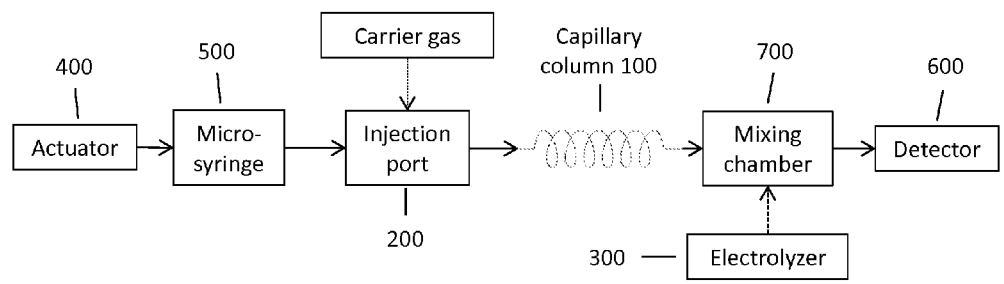
FIG. 7A is a flow diagram illustrating a method of using a miniaturized gas chromatograph.

FIGS. 1A and FIG. 1B illustrate an example miniaturized chromatographic system. FIG. 7A is a schematic illustrating the example miniaturized chromatographic system of FIGS. 1A and 1B. A sample is injected at sample injection port 200 via a micro-syringe 500 that is controlled by an actuator 400. In an alternative embodiment, sample introduction can be controlled by a valve rather than a micro-syringe. The sample can then be mixed with a carrier gas at the sample injection port 200, which can be hydrogen, oxygen, nitrogen, or any other carrier gas. The sample travels through the capillary column 100 and interacts with the medium that has coated or been inserted into the column. The sample then exits the capillary column 100 and travels to a mixing chamber 700 where it can be mixed with additional gases to prepare the sample for detection. For example, in one embodiment the detector is a flame ionization detector 600. In this embodiment, the sample that has exited the capillary column 100 can be mixed with a specified ratio of hydrogen and oxygen so that the sample can be combusted in the flame ionization detector. The hydrogen and oxygen gases can be produced from a nearby, miniature electrolyzer 300. The sample then passes through the flame ionization detector 600. The signal from the flame ionization detector is the output signal that can be used to determine the resultant chromatogram. In another embodiment, the detector can be a thermal conductivity detector, in which case it is not necessary to mix additional gasses after the sample exits the column (e.g., the column exits to the detector without mixing additional gasses). Each of the components 200, 600, 700 can be heated, for example by direct current joule heating. For example, if the column is made of fused silica, a wire can be wrapped around the column in order to heat the column through conduction and/or IR absorption. Alternatively, if the capillary column is made of steel or another conducting metal, the capillary column can be electrically isolated from the introduction port and detector and a direct current (or modulated direct current) can be applied to the capillary column, thereby heating the column. Traditionally, capillary columns are wound in a circle and adjacent loops directly contact each other. In order to prevent a short circuit while heating the column, each turn of the coil can be insulated from the adjacent turns. The insulation can be provided by winding the coil such than an air gap separates adjacent turns. Alternatively, one or more discrete insulating layers can separate adjacent turns. The entire system can be mounted on a printed circuit board 800. The printed circuit board includes a microprocessor that controls and monitors the electrical components of the system.

Figure 7B:
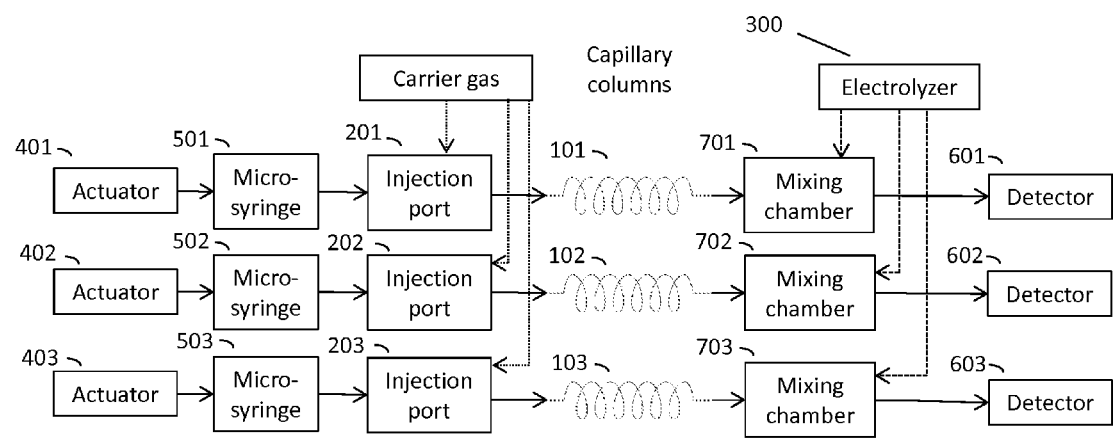
FIG. 7B is a flow diagram illustrating another method of using a miniaturized gas chromatograph.

FIG. 7B is a schematic illustrating the example miniaturized chromatographic system having a plurality of sample inputs. Each of the plurality of samples is injected at sample injection ports (201, 202, 203) via micro-syringes (501, 502, 503) that are controlled by actuators (401, 402, 403). The samples can then be mixed with a carrier gas at each of the sample injection ports (201, 202, 203). A common carrier gas supply can feed into each of the sample injection ports (201, 202, 203), or a separate carrier gas supply can be used for each sample. As above, the carrier gas can be hydrogen, oxygen, nitrogen, or any other carrier gas. The sample travels through the each of the capillary columns (101, 102, 103) and interacts with the medium that has coated or been inserted into the column. The sample then exits each of the capillary columns (101, 102, 103) and travels to the mixing chambers (701, 702, 703) where it can be mixed with additional gases to prepare the sample for detection. The detector can be a flame ionization detector (601, 602, 603). In this embodiment, the samples that has exited the capillary columns (101, 102, 103) can be mixed with a specified ratio of hydrogen and oxygen so that the sample can be combusted in the flame ionization detector. The hydrogen and oxygen gases can be produced from a nearby, miniature electrolyzer 300. In another embodiment, a plurality of miniature electrolyzers 300 can be employed. The sample then passes through the flame ionization detector 600. The signal from the flame ionization detector is the output signal that can be used to determine the resultant chromatogram. The remainder is as described with respect to the embodiment of FIGS. 1A, 1B, and 7A.

Figure 7C:
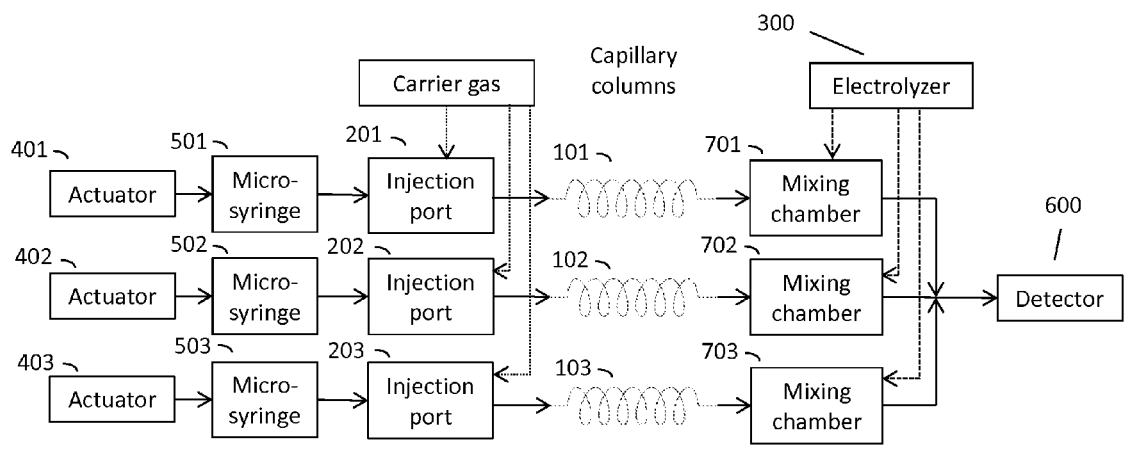
FIG. 7C is a flow diagram illustrating another method of using a miniaturized gas chromatograph.

FIG. 7C is a schematic illustrating the example miniaturized chromatographic system having a plurality of actuators (401, 402, 403), micro-syringes (501, 502, 503), injection ports (201, 202, 203), capillary columns (101, 102, 103), mixing chambers (701, 702, 703), along with an electrolyzer (300) and a detector (600). The remainder is as described with respect to the embodiment of FIGS. 1A, 1B, 7A, and 7B.

Figure 7D:
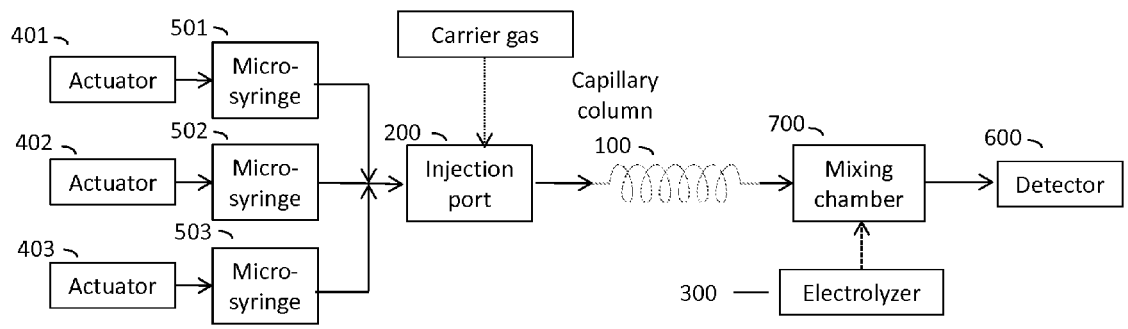
FIG. 7D is a flow diagram illustrating another method of using a miniaturized gas chromatograph.

FIG. 7D is a schematic illustrating the example miniaturized chromatographic system having a plurality of actuators (401, 402, 403) and micro-syringes (501, 502, 503) that utilize a single injection port (200), capillary column (100), mixing chamber (700), electrolyzer (300), and detector (600). The remainder is as described with respect to the embodiment of FIGS. 1A, 1B, 7A, 7B, and 7C.

Figure 2:
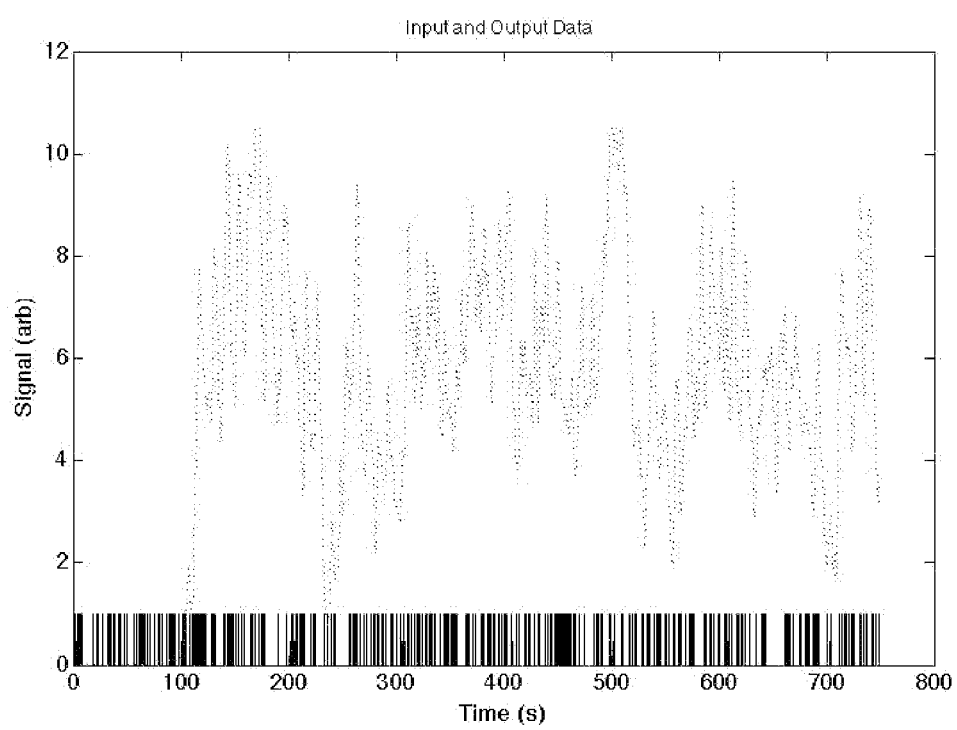
FIG. 2 illustrates a temporal sequence of the detector output when subject to a stochastic sequence controlling the sample introduction.
Figure 6:
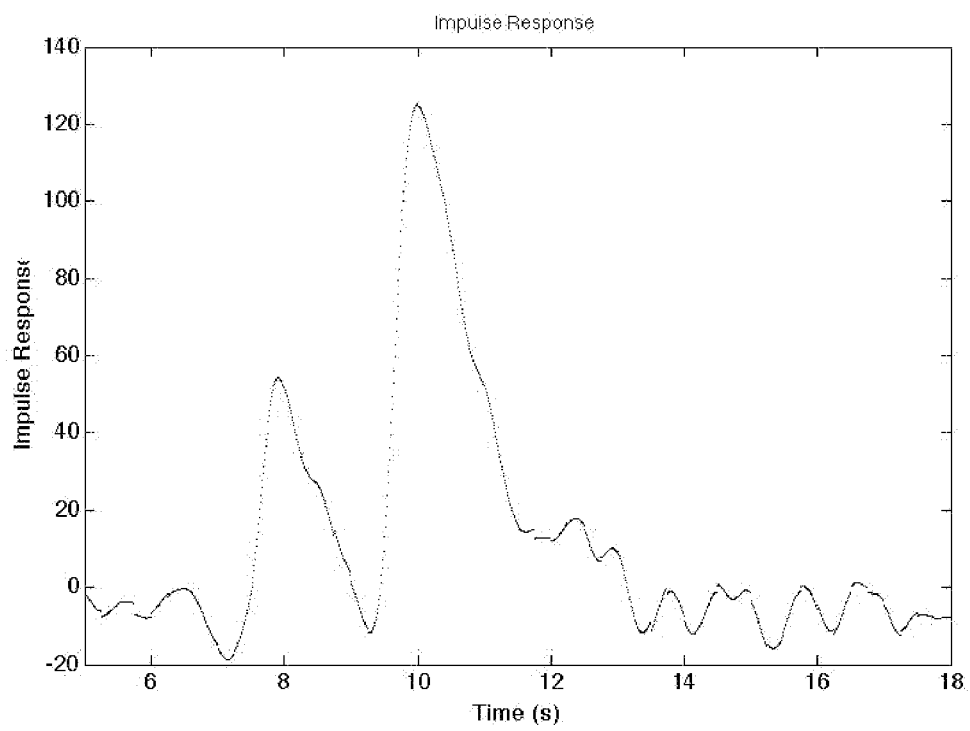
FIG. 6 illustrates an example graph of the impulse response of a two-eluent mixture of pentane and heptane with relative concentrations of 19% and 81%, respectively.

FIG. 2 illustrates the temporal sequence of a detector output when subject to a stochastic sequence controlling sample introduction. The solid lines at the bottom of the graph illustrate the stochastic input of 3 μL of a mixture of pentane and heptane into the gas chromatograph, whereby a value of one indicates a 3 μL injection and a value of zero indicates that no injection was made. The stochastic sequence was generated using the MATLAB random function with white noise, although the stochastic sequence can be generated by other known programming languages. The dotted line is the output from the detector prior to deconvolving the spectrum. Accordingly, the dotted line represents overlapping elution of the sample since the chromatograph is not completely cleared of sample between injections. FIG. 6 is the deconvolved output from FIG. 2, which shows a peak at approximately 8 seconds corresponding to pentane and a peak at approximately 10 seconds corresponding to heptane. In order to deconvolve the output signal of FIG. 2 to result in the chromatogram of FIG. 6 (e.g., a sample analysis), the mathematical operations described in Equations 1-4 were performed.

Figure 3:
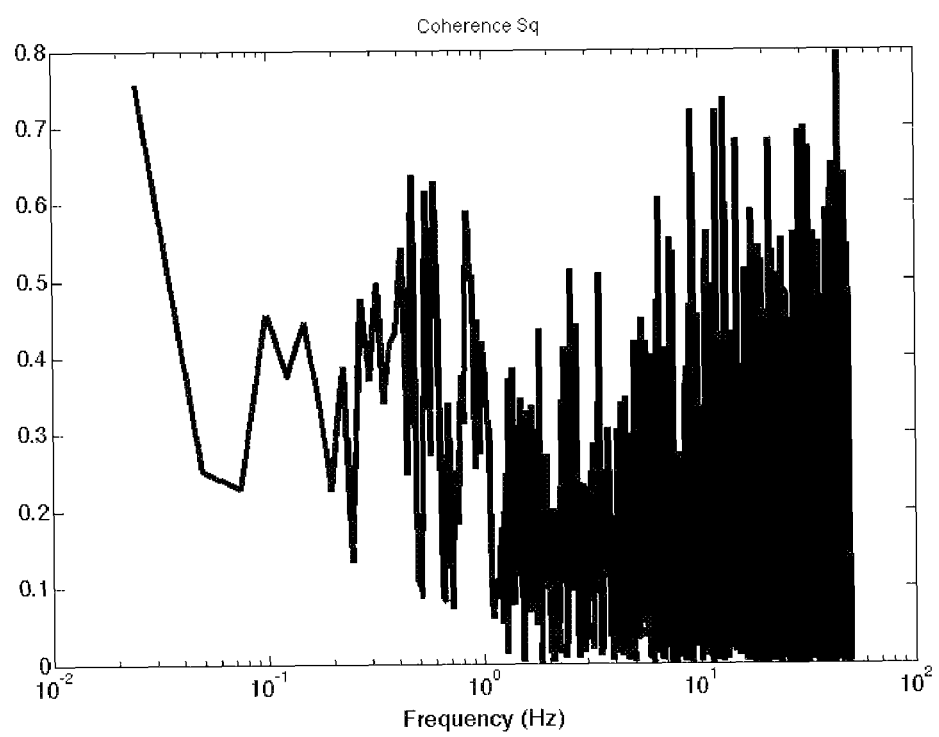
FIG. 3 illustrates an example coherence squared of the input and output.

FIG. 3 illustrates the coherence squared response of the system for the experiment of FIG. 2. The closer the coherence squared is to the value of 1, the more accurately the impulse response represents the system.

Figure 4A:
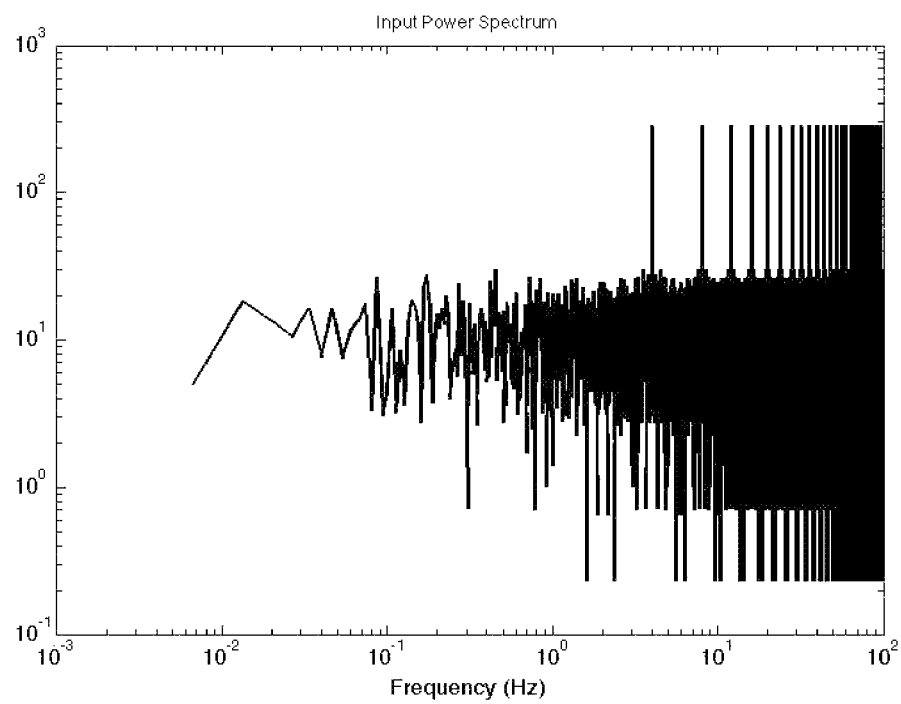
FIG. 4A illustrates an example graph of the input power spectrum.

FIG. 4A illustrates the input power spectrum of the system for the experiment of FIG. 2. The input power spectrum is generated by taking the discrete Fourier transform of the input signal. The input power spectrum describes how the power, from the input binary sequence, is distributed as a function of frequency. The relative uniformity of the input power spectrum indicates that the power is being delivered to the system relatively uniformly over the frequencies plotted. The frequency corresponds to the stochastic variable that is modulated as one of the system inputs. A non-uniform power spectrum would indicate that power is distributed more to certain frequencies, and less to other frequencies, or otherwise put, the input variable is modulated more at certain frequencies and less at other frequencies.

Figure 4B:
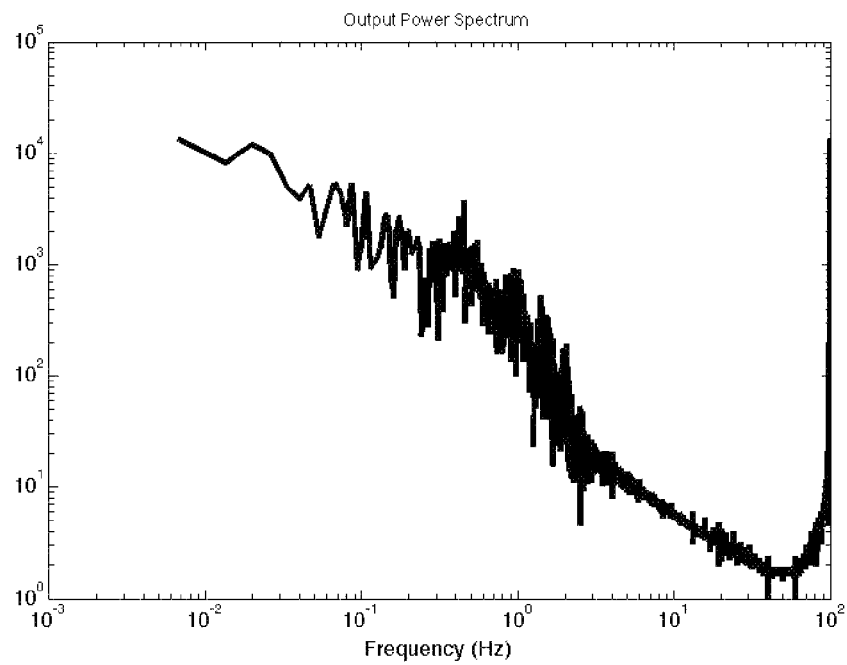
FIG. 4B illustrates an example graph of the output power spectrum.

FIG. 4B illustrates the output power spectrum of the system for the experiment of FIG. 2. The output power spectrum is generated by taking the discrete Fourier transform of the output signal. The output power spectrum describes how the power, from the output detector signal is distributed as a function of frequency. The decay of the output power spectrum, as plotted, indicates that the power of the system output signal is attenuated at higher frequencies. In other words, low frequency signals dominate the magnitude of output signal while high frequency signals contribute less to the magnitude of the output signal.

Figure 5A:
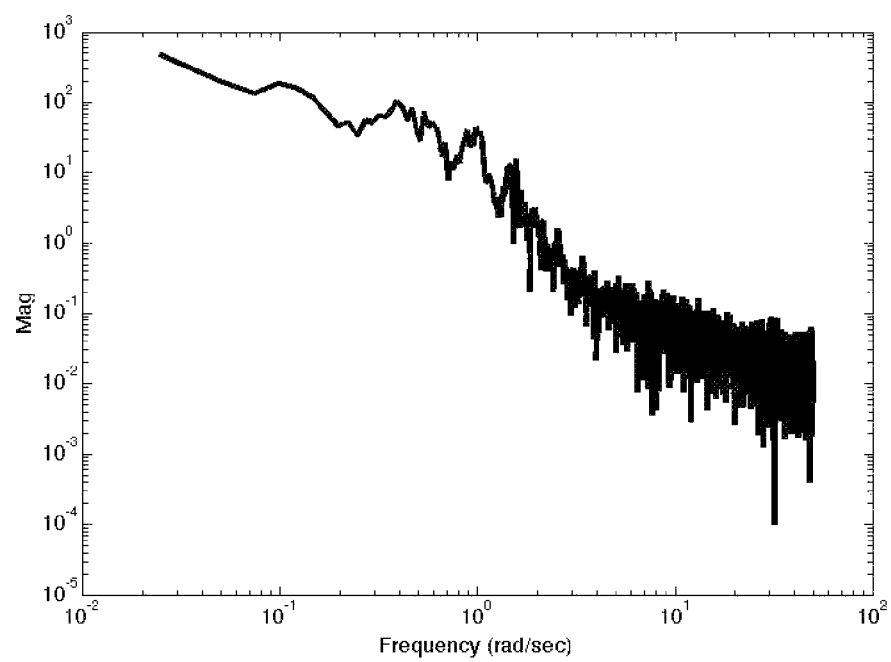
FIG. 5A illustrates an example graph of the magnitude of the chromatographic system.

FIG. 5A illustrates the magnitude component of the experimental Bode plot of the system for the experiment of FIG. 2. The magnitude corresponds to the magnitude of the frequency response gain. The gain can be defined as the ratio of the magnitude of the output signal to the input signal. The decay of the magnitude in FIG. 5A, as plotted, indicates that the system attenuates the input signal at higher frequencies.

Figure 5B:
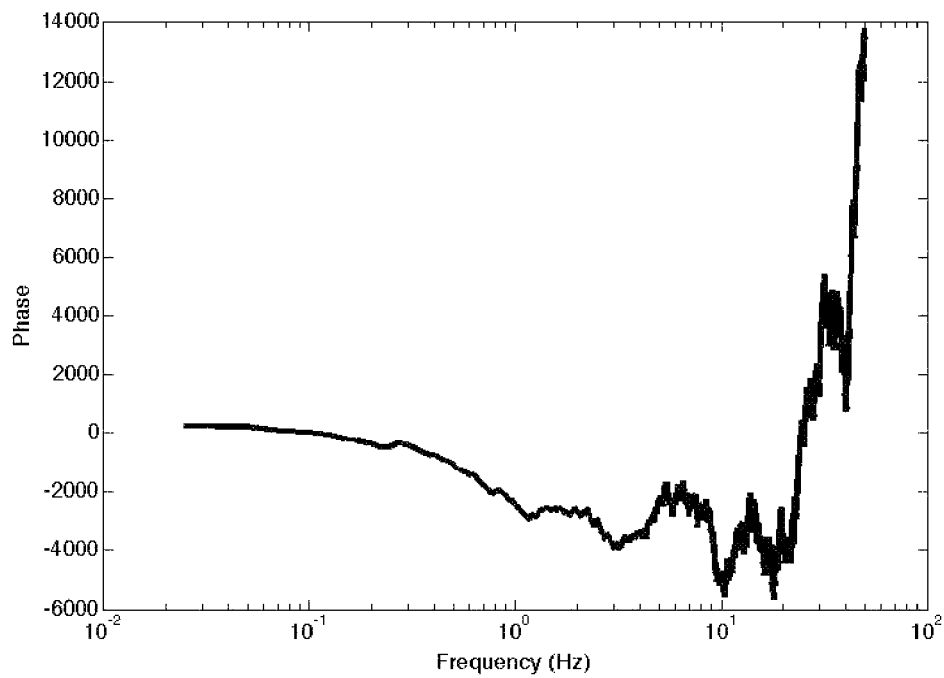
FIG. 5B illustrates an example graph of the phase of the chromatographic system.

FIG. 5B illustrates the phase component of the experimental Bode plot of the system for the experiment of FIG. 2. The phase corresponds to the phase shift between the output signal and the input single. The relatively uniformity of the phase at lower frequencies indicates that the phase of the system response is not affected by low input frequencies, but may be affected at higher frequencies. The phase between the input and the output signal shifts significantly at higher frequencies.

Equivalents

While this invention has been particularly shown and described with reference to example embodiments thereof, it will be understood by those skilled in the art that various changes in form and details may be made therein without departing from the scope of the invention encompassed by the appended claims.

Incorporation by Reference

The thesis titled "Development of Miniature, Continuous Measurement, Stochastic Perturbation Gas Chromatograph" (or any substantially similar title) by Eli Paster and submitted to the Department of Mechanical Engineering in Partial Fulfillment of the Requirements for the Degree of Doctor of Philosophy in Mechanical Engineering at the Massachusetts Institute of Technology is incorporated herein by reference in its entirety.

What is claimed is:

1. A method for performing chromatography, comprising:
   a) introducing a sample into a chromatography column;
   b) modulating sample volume according to a numerical value of a stochastic sequence ranging from zero to a predetermined value;
   c) detecting a sample output from the column; and
   d) processing the detected output with the stochastic sequence to provide a sample analysis.

2. The method of claim 1, wherein the numerical value corresponds to the total volume introduced.

3. The method of claim 1, wherein the numerical value indicates the volume per unit time at which the sample is introduced.

4. The method of claim 1, wherein the chromatography is gas chromatography.

5. The method of claim 1, wherein the chromatography is liquid chromatography.

6. The method of claim 1, wherein sample introduction is controlled by a plunger.

7. The method of claim 6, wherein the plunger is coupled with a linear actuator.

8. A system for performing chromatography, comprising:
   i) a sample introduction port;
   ii) a carrier gas source;
   iii) a capillary column in fluid communication with the sample introduction port and the carrier gas source;
   iv) a detector configured to detect a sample output from the capillary column; and
   v) a processor configured to modulate a column temperature with a stochastic input and to process the detected sample output with the stochastic input to provide a sample analysis.

9. A method for performing chromatography, comprising:
   a) introducing a sample into a chromatography column;
   b) modulating at least one variable with a stochastic input, wherein the variable is one or more of sample temperature, column temperature, column pressure, and switching of the sample between two or more chromatographic columns or mediums;
   c) detecting a sample output from the column; and
   d) processing the detected output with the stochastic input to provide a sample analysis.

10. The method of claim 9, wherein the variable modulated is sample temperature.

11. The method of claim 9, wherein the variable modulated is column temperature.

12. The method of claim 9, wherein the variable modulated is column pressure.

13. The method of claim 9, wherein the variable modulated is stochastic switching of the sample between two or more chromatographic columns or mediums.

14. The method of claim 9, wherein the chromatography is gas chromatography.

15. The method of claim 9, wherein the chromatography is liquid chromatography.

16. The method of claim 9, wherein sample introduction is controlled by a plunger.

17. The method of claim 16, wherein the plunger is coupled with a linear actuator.

* * * * *